United States Patent
Alberts et al.

(10) Patent No.: US 6,192,521 B1
(45) Date of Patent: Feb. 27, 2001

(54) PROCESS FOR MANUFACTURING SHORTS OR TROUSERS

(75) Inventors: Joseph Richard Alberts, Menasha; Edward Anthony Drezdzon, II, Appleton; Donald Merlin Fries, deceased, late of Combined Locks, by Sharon Fries, adminstratrix; Richard Mark Konetzke, Menasha; Thomas Theodore Kvitek, Menasha; Michael Joseph Muhlebach, Menasha; Michael Joseph Nelson, Neenah; Gerald Leigh Rabe, Appleton; Brendon Frank Ribble, Menasha; James Frederick Roth, Appleton; Jon Mark Wittmann, Combined Locks, all of WI (US)

(73) Assignee: Kimberly-Clark Worldwide, Inc., Neenah, WI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/841,961

(22) Filed: Apr. 8, 1997

(51) Int. Cl.$^7$ ........................................ A41D 1/06
(52) U.S. Cl. .............. 2/227; 2/228; 2/400; 604/358; 156/73.1
(58) Field of Search .............. 2/227, 228, 238, 2/400–408; 604/358, 374, 378, 379, 385.1, 385.2, 396; 156/60, 62.6, 73.1, 73.4, 181, 182, 184; 428/152, 156, 198, 68, 98

(56) References Cited

U.S. PATENT DOCUMENTS 3,338,992   8/1967   Kinney.
3,341,394   9/1967   Kinney.

(List continued on next page.)

FOREIGN PATENT DOCUMENTS

| 0 539 703 A1 | 5/1993 | (EP) | A61F/13/15 |
| 2 284 741 | 6/1995 | (GB) | A61F/13/15 |
| WO 95/18589 A1 | 7/1995 | (WO) | A61F/13/15 |
| WO 96/03949 A1 | 2/1996 | (WO) | A61F/13/15 |
| WO 96/03950 A1 | 2/1996 | (WO) | A61F/13/15 |
| WO 97/18785 A1 | 5/1997 | (WO) | A61F/13/15 |

OTHER PUBLICATIONS

Patent Cooperation Treaty Search Report from the International Search Authority, International Application No. PCT/US 98/06784 dated Jul. 2, 1998.

*Primary Examiner*—Gloria M. Hale
(74) *Attorney, Agent, or Firm*—Patricia A. Charlier

(57) ABSTRACT

The present invention relates to a continuous process for the manufacture of a shorts garment from four single layer webs of fabric, each web having two side edges. Two of the four webs are aligned in a side by side orientation. The side edges of the two webs are bonded together, defining a first composite web. The remaining two webs are aligned in a side by side orientation. The side edges of the two remaining webs are bonded together, defining a second composite web. The first and second composite webs are aligned together in a face to face orientation, defining an arrangement having two layers of fabric and two top side edges and two bottom side edges. The composite webs are intermittently bonded in an alternating orientation near the center of the webs. The interior portion of fabric is removed, defining a cavity. One pair of side edges are folded and bonded together. The other pair of side edges are folded and bonded together. The web of fabric is cut into discrete garment-sized pieces of fabric, each piece having at least two side seams, an inseam, two tubular leg structures and a waist opening.

18 Claims, 4 Drawing Sheets

U.S. PATENT DOCUMENTS

| | | |
|---|---|---|
| 3,502,763 | 3/1970 | Hartmann . |
| 3,542,615 | 11/1970 | Dobo et al. . |
| 3,692,618 | 9/1972 | Dorschner et al. . |
| 3,802,817 | 4/1974 | Matsuki et al. . |
| 3,849,241 | 11/1974 | Butin et al. . |
| 4,041,203 | 8/1977 | Brock et al. . |
| 4,327,448 | 5/1982 | Lunt .......................................... 2/404 |
| 4,340,563 | 7/1982 | Appel et al. . |
| 4,388,075 | 6/1983 | Mesek et al. . |
| 4,405,297 | 9/1983 | Appel et al. ......................... 425/72 S |
| 4,606,964 | 8/1986 | Wideman ............................. 428/152 |
| 4,639,949 | 2/1987 | Ales et al. ............................... 2/400 |
| 4,657,802 | 4/1987 | Morman .............................. 428/152 |
| 4,720,415 | 1/1988 | Vander Wielen et al. ........... 428/152 |
| 4,798,603 | 1/1989 | Meyer et al. ......................... 604/378 |
| 4,938,753 | 7/1990 | Van Gompel et al. ........... 604/385.2 |
| 4,938,754 | 7/1990 | Mesek ................................ 604/385.2 |
| 4,940,464 | 7/1990 | Van Gompel et al. ............... 604/396 |
| 5,114,781 | 5/1992 | Morman ............................... 428/198 |
| 5,116,662 | 5/1992 | Morman ............................... 428/198 |
| 5,145,727 | 9/1992 | Potts et al. ........................... 428/198 |
| 5,169,706 | 12/1992 | Collier, IV et al. ................. 428/152 |
| 5,178,931 | 1/1993 | Perkins et al. ....................... 428/198 |
| 5,188,885 | 2/1993 | Timmons et al. .................... 428/198 |
| 5,340,424 * | 8/1994 | Matsushita ............................... 2/400 |
| 5,711,832 * | 1/1998 | Glaug et al. ............................. 2/401 |

* cited by examiner

PROCESS FOR MANUFACTURING SHORTS OR TROUSERS

BACKGROUND OF THE INVENTION

This invention pertains to a process for manufacturing garments, and more particularly to a cost effective, high speed method for manufacturing shorts or trousers.

Typically, the construction of trousers or shorts employs a multi-step process using multiple pieces of fabric, such as cloth or woven materials. The pieces of fabric are cut from a larger bolt of fabric into specified shapes. The pieces are sewn together, forming a finished garment. This process is labor and time intensive.

In the area of disposable garments, such as children bibs, coveralls, or examinations gowns, a more continuous process is used. Material, such as paper or plastic, is unwound from a roll. Strategically placed cuts are made in the material, forming head, arms, or legs openings. However, these disposable garments have several limitations, both in the design and durability necessary for active wear garments.

SUMMARY OF THE INVENTION

Thus, there is a need to provide an improved process for manufacturing garments, including washable and disposable garments. There is also a need to provide comfortable and inexpensive active or swim wear garments.

In addition, the garments need to be easy to put on and durable during wear. In response to this need, an improved cost effective, high speed process for manufacturing shorts and trousers has been discovered.

One embodiment of the present invention is a continuous process for the manufacture of shorts or trousers to be worn about the lower body comprising an outer surface and an opposing inner surface, defining a waist opening and two leg openings. The present invention combines at least one web of fabric in a single continuous process to create shorts or trousers. Seaming can be accomplished by use of ultrasonics, heat sealing, adhesives, tape, or sewing, each offering a unique modification to the process.

The present invention relates to a continuous process for the manufacture of a shorts garment comprising:
 a. providing four single layer webs of fabric including two side edges on each web of fabric;
 b. aligning two of the four webs together in a side by side orientation;
 c. bonding one side edge of each of the two webs in the side by side orientation together, defining at least a portion of an inseam and a first composite web;
 d. aligning the remaining two of the four webs together in a side by side orientation;
 e. bonding one side edge of each of the two webs in the side by side orientation together, defining at least another portion of the inseam and a second composite web;
 f. aligning the first and second composite webs together in the face to face orientation, defining a arrangement having two layers of fabric and two top side edges and two bottom side edges;
 g. intermittently bonding the composite webs wherein the bonding is accomplished in an alternating orientation near the center of the webs, defining center seams having a specific shape and an interior portion of fabric;
 h. removing the interior portion of fabric, defining a cavity having a front to back contour to accommodate a human body;
 i. folding one pair of the side edges together;
 j. bonding the pair of side edges, defining at least one side seam and a tubular leg structure;
 k. folding the other pair of side edges together;
 l. bonding the other pair of side edges, defining at least another side seam and another tubular leg structure; and,
 m. cutting the single web of fabric, defining discrete garmentsized pieces of fabric wherein each piece of fabric includes at least two side seams, an inseam, two tubular leg structures, and a waist opening.

Numerous features and advantages of the present invention will appear from the following description. In the description, reference is made to the accompanying drawings which illustrate desired embodiments of the invention. Such embodiments do not represent the full scope of the invention. Reference should, therefore, be made to the claims herein for interpreting the full scope of the invention.

BRIEF DESCRIPTION OF THE DRAWINGS

The above-mentioned and other features of the present invention and the manner of attaining them will become more apparent, and the invention itself will be better understood by reference to the following description of the invention, taken in conjunction with the accompanying drawings, wherein.

Definitions

Figure 1:
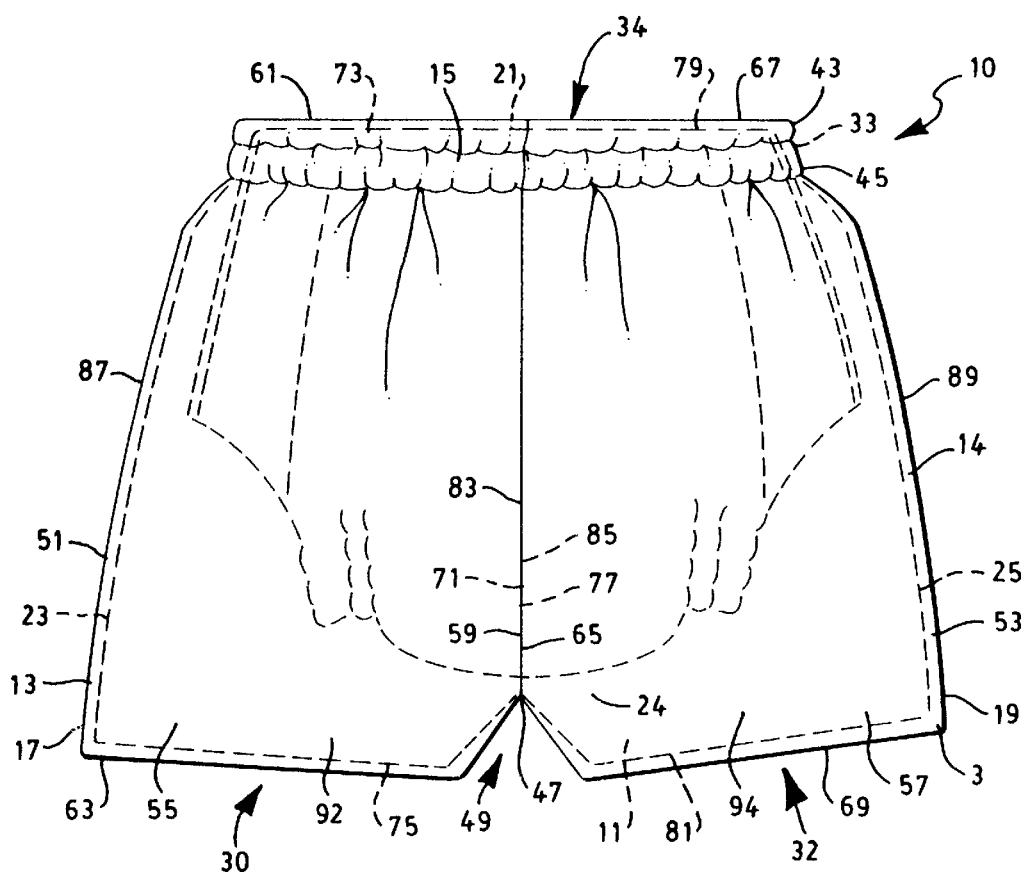
FIG. 1 is a front view of a garment made by the present invention.

Within the context of this specification, each term or phrase below will include the following meaning or meanings:
 (a) "Bonded" refers to the joining, adhering, connecting, attaching, or the like, of two elements. Two elements will be considered to be bonded together when they are bonded directly to one another or indirectly to one another, such as when each is directly bonded to intermediate elements.
 (b) "Bonded Carded Fabric or Web" refers to fabric or webs made from staple fibers which are sent through a combing or carding unit, which breaks apart and aligns the staple fibers in the machine direction to form a generally machine direction-oriented fibrous nonwoven web. Such fibers are usually purchased in bales which are placed in a picker which separates the fibers prior to the carding unit. Once the web or fabric is formed, it is then bonded by one or more of several known bonding methods. Once such bonding method is powder bonding, wherein a powdered adhesive is distributed through the web or fabric and then activated, usually by heating the fabric and adhesive with hot air. Another suitable bonding method is pattern boding, wherein heated calendar rolls or ultrasonic bonding equipment are used to bond the fibers together, usually in a localized bond pattern, though the fabric can be bonded across its entire surface if so desired. Another suitable and well-known bonding method, particularly when using bi-component staple fibers, is through-air bonding.

(c) "Cross Machine Direction" means a direction generally perpendicular to the machine direction.

(d) "Disposable" includes being disposed of after use, and not intended to be washed and reused.

(e) "Disposed", "disposed on", "disposed with", "disposed at", "disposed near", and variations thereof are intended to mean that one element can be integral or unitary with another element, or that one element can be a separate structure joined to or connected to or placed with or placed near another element.

(f) "Elasticity" and "elastic" include that property of a material by virtue of which it tends to substantially recover to its original size and shape after removal of a force causing deformation of the material.

(g) "Elastically connected" and "elastically connecting" refer to two elements being separated by and bonded to an elastic member, where the relative position of the two elements may change due to extension of the elastic member.

(h) "Elongation" includes the ratio of the extension of a material to the length of a material prior to the extension. Elongation is expressed in percent.

(i) "Extension", "extend", and "extended" include the change in length of a material due to stretching. Extension is expressed in units of length.

(j) "Fabric" is used to refer to all of the woven, knitted, and nonwoven webs.

(k) "Flexible" refers to materials or fabrics that are compliant and readily conform to the general shape and contours of an individual's body.

(l) "Force" includes a physical influence exerted by one body on another which produces acceleration of bodies that are free to move and deformation of bodies that are not free to move. Force is expressed in grams-force.

(m) "Foreshortened" and "foreshortening" include to shorten beforehand, that is, before a subsequent step.

(n) "Front" and "back" are used to designate relationships relative to the garment itself, rather than to suggest any position the garment assumes when it is positioned on a wearer.

(o) "Gatherable" material is one which, when bonded to the reticular web with the latter under tension, will gather, with the formation of puckers or gathers, to accommodate contraction of the reticulated web upon release of the tensioning forces.

(p) "Machine Direction" means the direction in which it is produced or the length of fabric moving in the direction of the machine operations.

(q) "Meltblown Fibers" means fibers formed by extruding a molten thermoplastic material through a plurality of fine, usually circular, die capillaries as molten threads or filaments into converging high velocity, usually hot gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example in U.S. Pat. No. 3,849,241 to Butin, et al. Meltblown fibers are microfibers which may be continuous or discontinuous, are generally smaller than 10 microns in average diameter, and are generally tacky when deposited onto a collecting surface.

(r) "Member" when used in the singular can have the dual meaning of a single element or a plurality of elements.

(s) "Multi-layer Laminate" means a laminate wherein some of the layers are spunbond and some are meltblown such as a spunbond/meltblown/spunbond (SMS) laminate and other as disclosed in U.S. Pat. No. 4,041,203 to Brock et al., U.S. Pat. No. 5,169,706 to Collier et al., U.S. Pat. No. 5,145,727 to Potts et al., U.S. Pat. No. 5,178,931 to Perkins, et al., and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (6 to 400 gsm), or more particularly from about 0.75 to about 3 osy. Multi-layer laminates may also have various numbers of meltblown layers or multiple spunbond layers in may different configurations and may include other materials like films or coform materials.

(t) "Nockable Material" means any material which can be necked.

(u) "Necked Material" refers to any material which has been constricted in at least one dimension by processes such as, for example, drawing or gathering.

(v) "Non-elastic" or "Inelastic" refers to any material that does not fall within the definition of "elastic".

(w) "Nonwoven fabric or web" means a web having a structure of individual fibers or threads which are interlaid, but not in an identifiable manner as in a knitted fabric. Nonwoven fabrics or webs have been formed from many processes such as, for example, meltblowing processes, spunbonding processes, and bonded carded web processes. The basis weight of nonwoven fabrics is usually expressed in ounces of material per square yard (osy) or grams per square meter (gsm) and the fiber diameters are usually expressed in microns.

(x) "Operatively joined" with reference to the attachment of an elastic member to another element means that the elastic member when attached to or connected to or treated with heat with the element gives that element elastic properties. With reference to the attachment of a non-elastic member to another element, it means that the member and element can be attached in any suitable manner that permits or allows them to perform the intended or described function of the joinder. The joining, attaching, connecting or the like can be either directly, such as joining either member directly to an element, or can be indirectly by means of another member or element disposed between the first member and the first element.

(y) "Pattern" includes any geometric or non-geometric form that can include, among others, a series of connected or unconnected lines or curves, a series of parallel or nonparallel or intersecting lines or curves, a series of linear or curvilinear lines, and the like, or any combinations thereof. The pattern can include a repeating form and/or non-repeating form.

(z) "Rupture" includes the breaking or tearing apart of a material. In tensile testing, rupture refers to the total separation of a material into two parts, either all at once or in stages, or the development of a hole in some materials.

(aa) "Stretch bonded" refers to an elastomeric strand being bonded to another member while the elastomeric strand is elongated at least about 25 percent of its relaxed length. Desirably, the term "stretch bonded" refers to the situation wherein the elastomeric strand is elongated at least about 50 percent, more desirably at least about 300 percent, of its relaxed length when it is bonded to the other member.

(bb) "Stretch bonded laminate" ("SBL") refers to a composite material having at least two layers in which one layer is a gatherable layer and the other layer is a stretchable, that is, elastic, layer. The layers are joined together when the stretchable layer is in a stretched condition so that upon relaxing the layers, the gatherable layer is gathered.

(cc) "Spunbonded fibers" refers to small diameter fibers which are formed by extruding molten thermoplastic material as filaments from a plurality of fine, usually circular capillaries or spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. No. 3,338,992 and U.S. Pat. No. 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns.

(dd) "Tension" includes a uni-axial force tending to cause the extension of a body or the balancing force within that body resisting the extension.

(ee) "Two-dimensional" refers to a garment, such as a diaper, that can be opened and laid in a flat condition without destructively tearing any structure. This type of garment does not have continuous leg and waist openings when opened and laid flat, and requires a fastening device, such as adhesive tapes, to attach the garment about the wearer.

(ff) "Three-dimensional" refers to a finished garment similar to shorts or pants in that they have continuous leg and waist openings that are bounded by the material of which the garment is made. This type of garment can be opened and laid flat only by destructively tearing it. This type of garment may or may not have manually tearable seams.

(gg) "Ultimate elongation" includes the elongation at the point of rupture.

These definitions are not intended to be limiting and these terms may be defined with additional language in the remaining portion of the specification.

DETAILED DESCRIPTION

Figure 2:
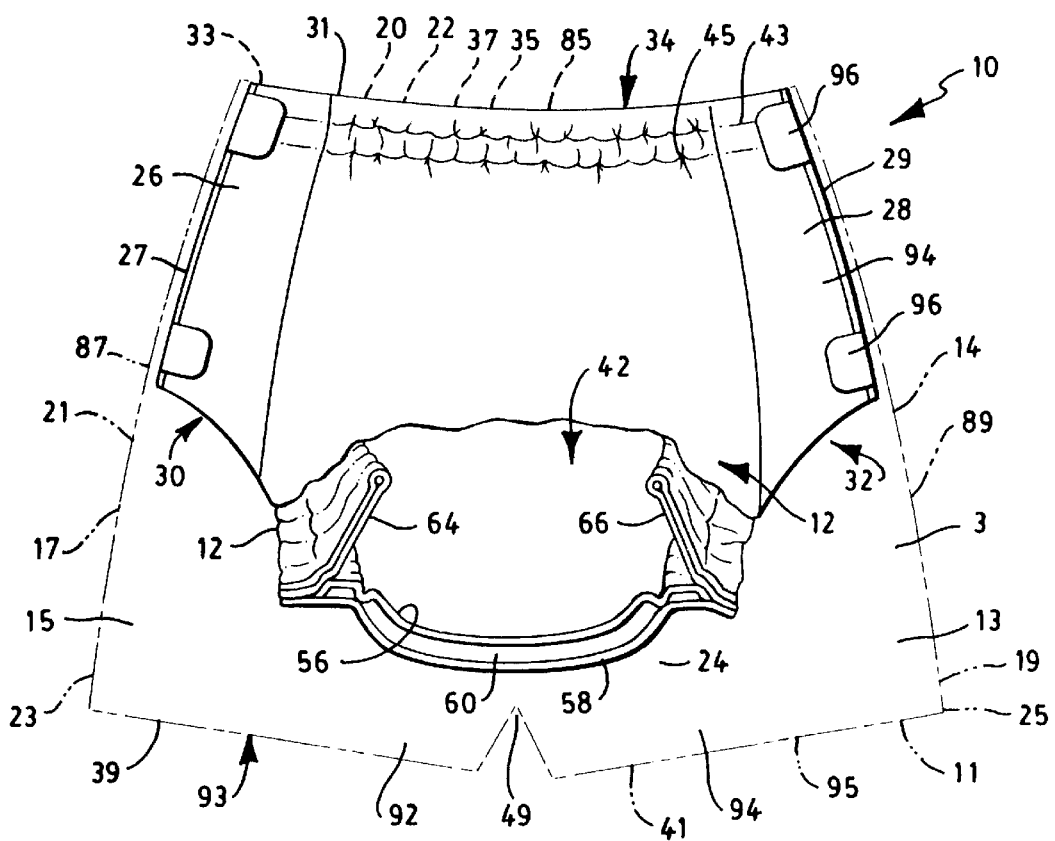
FIG. 2 is a front cut-away view of a garment with a waste containment structure made by the present invention.

The garment 10 is illustrated in FIGS. 1 and 2. The shorts 14 includes opposing inner and outer surfaces 11 and 13. Within this application, the term "shorts" is understood to mean shorts, trousers, or any type of boxer styled garment having variable lengths of leg coverings. According to the desired embodiment, see FIG. 1, the shorts 14 of the garment 10 desirably comprises a right front panel 51, a left front panel 53, a right back panel 55; and a left back panel 57. The right front panel 51 has a pair of side edges 17 and 59 and opposing waist region 61 and bottom edge 63 positioned between the side edges 17 and 59. The left front panel 53 has a pair of side edges 19 and 65 and opposing waist region 67 and bottom edge 69 positioned between the first side edges 19 and 65.

The right back panel 55 has a pair of side edges 23 and 71 and opposing waist region 73 and bottom edge 75 positioned between the side edges 23 and 71. The left back panel 57 has a pair of side edges 25 and 77 and opposing waist region 79 and bottom edge 81 positioned between the first side edges 25 and 77.

The side edge 59 is joined to the side edge 65 at the center seam 83 forming a front waist region 31 and a front panel 15. The side edge 71 is joined to the side edge 77 at the center seam 85 forming a back waist region 33 and a back panel 21. The side edge 17 is joined to the side edge 23 at the side seam 87 and the side edge 19 is joined to the side edge 25 at the side seam 89.

The front panel 15 and the back panel 21 of the shorts 14 are joined together at the inseam 47 so as to define a crotch section 49 extending centrally between the front and back panels 15 and 21 respectively. The front panel 15, the back panel 21, and the crotch section 49 when joined together define a waist opening 34, and two leg openings 93 and 95 at opposite sides of the crotch section 49.

In the embodiments of the garment 10 where a pant structure 12 is not included, the waist regions 31 and 33 are joined to waist elastic members 43 and 45 on the inner surface 11 of the shorts 14. Although not as desirable, the waist elastic members 43 and 45 could be joined to the outer surface 13 of the shorts 14.

The waist elastic members 43 and 45 may be stretch bonded to the first and second waist regions 31 and 33 of the shorts 14 or bonded in a relaxed state to a gathered portion the waist regions 31 and 33 of the shorts 14. One suitable method for attaching the waist elastics 43 and 45 is disclosed in U.S. Pat. No. 4,639,949 issued Feb. 7, 1987, to Ales et al., which is incorporated herein by reference.

Desirably, the waist elastic members 43 and 45 are made up of at least two spunbond layers with elastic positioned between the spunbond layers. The first and second waist regions 31 and 33 and the waist elastic members 43 and 45 are desirably bonded together by adhesives, however other methods of bonding discussed above can be utilized. The first and second waist regions 31 and 33 of the shorts 14 may be attached to the waist elastic members 43 and 45 around the entirety of the waist opening 34 or only a portion thereof.

The first and second waist regions 31 and 33 end at the top edge or near the top edge of the waist elastic members 43 and 45. This allows the first and second waist regions 31 and 33 to be cut off simultaneously. The bottom edges 63, 69, 75, and 81 can be hemmed. For easier manufacture, the bottom edges 63, 69, 75; and 81 are left unhemmed, facilitating easy machine cutoff.

In some embodiments of the garment 10, the side seams 87 and 89, the center seams 83 and 85, and the inseam 47 are non-refastenable. Non-refastenable seams may be formed by any suitable means such as ultrasonic sealing, adhesive bonding, heat sealing, sewing, tape, or the like. One suitable methods of forming such seams is disclosed in U.S. Pat. No. 4,938,753 issued Jul. 3, 1990, to Van Gompel et al., which is incorporated herein by reference. As illustrated most clearly in FIG. 1, the non-refastenable side seams 87 and 89, the center seams 83 and 85, and the inseam 47 may be bonded together to form non-refastenable seams.

In other embodiments of the garment 10, the side seams 87 and 89, the center seams 83 and 85, and the inseam 47 are refastenable. Refastenable means for securing edges include adhesives and mechanical type fasteners 96 see (FIG. 2). Mechanical type fasteners include buttons, button holes, snaps, buckles, clasps, hooks and loops, end extensions, tabs, and the like which are designed or adapted to interlock or engage some type of complimentary device or the inner surface 11 or outer surface 13 of the garment 10. In addition, elasticized fasteners may also be used in assuring better fit of the garment 10.

According to another embodiment of the garment 10, see FIG. 2, the shorts 14 of the garment 10 desirably comprise a front panel 15 and a back panel 21. The front panel 15 has a pair of side edges 17 and 19 and opposing waist region 31 and bottom edge 39 positioned between the side edges 17 and 19. The back panel 21 has a pair of side edges 23 and 25 and opposing waist region 33 and bottom edge 41 positioned between the side edges 23 and 25. The side edge 17 is joined to the side edge 23 at the side seam 87 and the side edge 19 is joined to the side edge 25 at the side seam 89.

The front panel 15 and the back panel 21 of the shorts 14 are joined together at the inseam 47 so as to define a crotch section 49 extending centrally between the front and back panels 15 and 21, respectively. The front panel 15, the back panel 21, and the crotch section 49 when joined together define a waist opening 34, and two leg openings 93 and 95 at opposite sides of the crotch section 49.

In the embodiments of the garment 10 where a pant structure 12 is not included, the waist regions 31 and 33 are joined to waist elastic members 43 and 45 on the inner surface 11 of the shorts 14. Although not as desirable, the waist elastic members 43 and 45 could be joined to the outer surface 13 of the shorts 14.

The waist elastic members 43 and 45 may be stretch bonded to the first and second waist regions 31 and 33 of the shorts 14 or bonded in a relaxed state to a gathered portion the waist regions 31 and 33 of the shorts 14. One suitable method for attaching the waist elastics 43 and 45 is disclosed in U.S. Pat. No. 4,639,949 issued Feb. 7, 1987, to Ales et al., which is incorporated herein by reference.

Desirably, the waist elastic members 43 and 45 are made up of at least two spunbond layers (See FIGS. 1 and 2) with elastic positioned between the spunbond layers. The first and second waist regions 31 and 33 and the waist elastic members 43 and 45 are desirably bonded together by adhesives, however other methods of bonding discussed above can be utilized. The first and second waist regions 31 and 33 of the shorts 14 may be attached to the waist elastic members 43 and 45 around the entirety of the waist opening 34 or only a portion thereof.

The first and second waist regions 31 and 33 end at the top edge or near the top edge of the waist elastic members 43 and 45. This allows the first and second waist regions 31 and 33 to be cut off simultaneously. The bottom edges 39 and 41 can be hemmed. For easier manufacture, the bottom edges 39 and 41 are left unhemmed, facilitating easy machine cutoff.

The garment 10 can be formed in a continuous process by supplying a cover material including individual portions that define a single cover having waist regions 31 and 33 and front and back panels 15 and 21 extending from the waist regions 31 and 33. The crotch section 49 is formed between the front and back panels 15 and 21. The panels 15 and 21 can be shaped by die cutters, water jet cutters or other suitable means.

In some embodiments of the garment 10, the side seams 87 and 89 and inseam 47 are non-refastenable. Non-refastenable seams may be formed by any suitable means such as ultrasonic sealing, adhesive bonding, heat sealing, sewing, tape, or the like as discussed above.

In other embodiments of the garment 10, the side seams 87 and 89 and inseam 47 are refastenable. Refastenable means for securing the edges include adhesives and mechanical type fasteners. See the discussion 35 above.

The pant structure 12 includes a front and back longitudinally spaced waist band regions 20 and 22, which terminate in longitudinal ends 35 and 37 of the pant structure 12. A crotch area 24 is located between the front waist band region 20 and the back band waist region 22. The left side panel 26 and the right side panel 28 extend between the front waist region 20 and the back waist region 22. The pant structure 12 may include a waste containment section 42. The waste containment structure 42 may include a backsheet 58, a bodyside liner 56, an absorbent core 60 as well as the side panels 26 and 28. In some embodiments, containment flaps 64 and 66 are included in the waste containment structure 42.

Side panels 26 and 28, which may or may not have elastic elements, are ultrasonically bonded and are formed such that the materials of construction provide a manually tearable, non-refastenable region near the seams 27 and 29. The side panels 26 and 28 can incorporate elastic elements which include incorporating a layer of elastic material or an SBL.

In some embodiments of the garment 10, the side seams 27 and 29 are nonrefastenable. Non-refastenable seams may be formed by any suitable means such as ultrasonic sealing, adhesive bonding, heat sealing, sewing, tape, or the like. One suitable methods of forming such seams is disclosed in U.S. Pat. No. 4,938,753 issued Jul. 3, 1990, to Van Gompel et al., which is incorporated herein by reference. As illustrated most clearly in FIG. 1, the non-refastenable side seams 27 and 29 may be bonded together to form non-refastenable seams.

In other embodiments of the garment 10, the side seams 27 and 29 are refastenable. Refastenable means for securing edges include adhesives and mechanical type fasteners 96 (see FIG. 2). Mechanical type fasteners include buttons, button holes, snaps, buckles, clasps, hooks and loops, end extensions, tabs, and the like which are designed or adapted to interlock or engage some type of complimentary device or the inner surface 11 or outer surface 13 of the garment 10. In addition, elasticized fasteners may also be used in assuring better fit of the garment 10.

Figure 3:
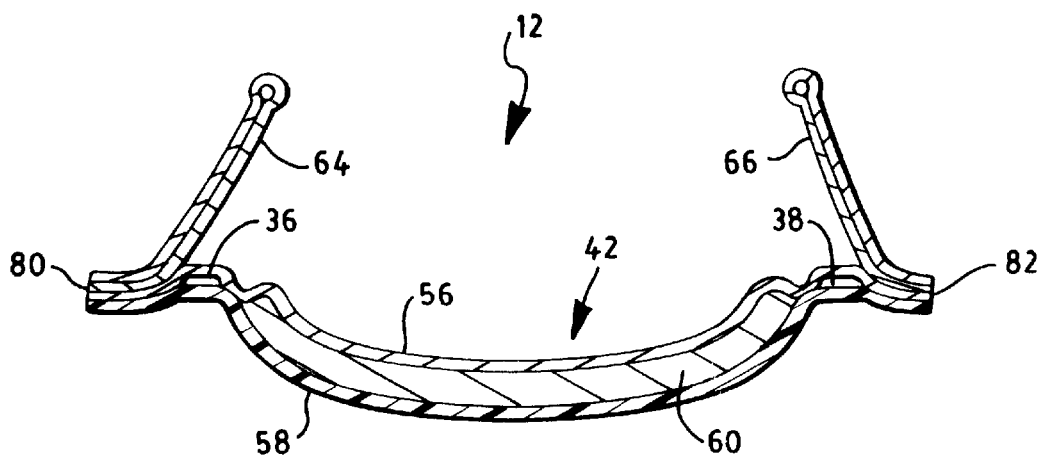
FIG. 3 is a cross sectional view of a waste containment structure.

The pant structure 12 also desirably includes leg elastics 36 and 38 operatively joined to the backsheet 58, the bodyside liner 56, or both (See FIGS. 2 and 3). The leg elastics 36 and 38 are positioned along the edges of side panels 26 and 28 and the longitudinal edges 80 and 82 of the pant structure 12 or the waste containment structure 42 in the crotch area 24. The leg elastics 36 and 38 may assist in holding the pant structure 12, and ultimately the waste containment structure 42, where present, against the body of the wearer or forming seals or gaskets about the legs of the wearer.

Leg elastics 36 and 38 can be stretch bonded to the cover material along the longitudinal edges of the pant structure 12. The waist elastic 43 and 45 elasticizes the front and back waist band regions 20 and 22 of the pant structure 12. Thereafter, each side panel 26 and 28 can be bonded together by seams 27 and 29 so that the pant structure 12 defines the waist opening 34 and the pair of leg openings 30 and 32.

The pant structure 12 and the shorts 14 are joined at the waist of the garment 10 (See FIGS. 1 and 2). The longitudinal ends 35 and 37 of the waist band regions 20 and 22 of the pant structure 12 are joined to the waist regions 31 and 33. Waist elastic members 43 and 45 are positioned between the longitudinal ends 35 and 37 and the waist regions 31 and 33. The pant structure 12 is desirably attached to the front panel 15 and the back panel 21, but not to the crotch section 49 of the shorts 14.

Desirably, the waist elastic members 43 and 45 are made up of at least two spunbond layers with elastic positioned between the spunbond layers. The longitudinal ends 35 and 37, waist regions 31 and 33, and the waist elastic members 43 and 45 are desirably bonded together by adhesives, however other methods of bonding discussed above can be utilized. The waist regions 31 and 33 of the shorts 14 may be attached to the pant structure 12 around the entirety of the waist opening 34 or only a portion thereof. The waist elastic members 43 and 45 may be stretch bonded to the shorts 14 or bonded in a relaxed state to a gathered portion of the waist regions of the panels of the shorts 14.

The waist elastic members 43 and 45 may be stretch bonded to the waist regions 20 and 22 of the shorts 14 and the waist band regions 20 and 22 of the pant structure 12 or bonded in a relaxed state to a gathered portion of the waist band regions 20 and 22 of the pant structure 12 and the waist regions 31 and 39 of the shorts 14. One suitable method for attaching the waist elastics 43 and 45 is disclosed in U.S. Pat. No. 4,639,949 issued Feb. 7, 1987, to Ales et al., which is incorporated herein by reference.

The longitudinal ends 35 and 37 and the waist regions 31 and 33 end at the top edge or near the top edge of the waist elastic members 43 and 45. This allows the longitudinal ends 35 and 37 and the waist regions 31 and 33 to be cut off simultaneously.

The garment 10 may include a waste containment structure 42. With reference to FIG. 2, the waste containment structure 42 as illustrated includes a backsheet 58, a substantially liquid permeable bodyside liner 56, and an absorbent core 60 sandwiched between the backsheet 58 and the bodyside liner 56. The backsheet 58 and bodyside liner 56 are desirably longer and wider than the absorbent core 60, so that the peripheries of the backsheet 58 and liner 56 form margins which may be sealed together using ultrasonic bonds, thermal bonds, adhesives, tape, or other suitable means. The absorbent core 60 may be attached to the backsheet 58 and/or the bodyside liner 56 using ultrasonic bonds, adhesives, tape, sewing, or other suitable means.

The waste containment structure 42 may also include additional components to assist in the acquisition, distribution and storage of waste material. For example, the waste containment structure 42 may include a transport layer, such as described in U.S. Pat. No. 4,798,603 issued Jan. 17, 1989, to Meyer et al., or a surge management layer, such as described in European Patent Application EP 0 539 703 A1, published May 5, 1993, which patent and application are incorporated herein by reference.

The waste containment structure 42 can be constructed by supplying bodyside liner and backsheet materials and sandwiching an individual absorbent core 60 between the backsheet 58 and bodyside liner 56. The side peripheries of the backsheet 58 and bodyside liner 56 outward of the absorbent core 60 can be joined with side panel material and sealed together. Individual waste containment structure 42 can then be cut from the continuous supply of backsheet and bodyside liner materials. The waste containment structure 42 may optionally be T-shaped, I-shaped, hourglassshaped, or irregularly-shaped.

The absorbent core 60 can comprise a coform material composed of a mixture of cellulosic fibers and synthetic polymer fibers. For example, the coform material may comprise an airlaid blend of cellulosic wood fibers and meltblown polyolefin fibers, such as polyethylene or polypropylene fibers. Absorbent core 60 can comprise only coform, or a combination of superabsorbent materials and coform, with other absorbent or non-absorbent materials.

The coform material may comprise an airlaid blend of cellulosic wood fibers and meltblown polyolefin fibers, such as polyethylene or polypropylene fibers, or may comprise an air-formed batt of cellulosic fibers (i.e., wood pulp fluff). Optionally, the absorbent core 60 may be treated with a surfactant to aid in liquid acquisition when in a dry environment. In particular embodiments of the invention, the absorbent core 60 has a bulk thickness of not more than about 1.25 cm when dry. The hydrophilic fibers and polymer strands may be provided in a fiber-topolymer ratio which is less than 80:20, for example between about 30:70 and about 80:20 and, desirably between about 60:40 and about 70:30.

For absorbent core 60, compounds to increase the core absorbency, are included in an effective amount and may consist of organic or inorganic high-absorbency materials. For example, the absorbent core 60 can include 0–5 weight percent high-absorbency material, desirably less than 1%. Suitable inorganic high-absorbency materials include, for example, absorbent clays and silica gels.

Organic high-absorbency materials can include natural materials, such as pectin, guar gum and peat moss, as well as synthetic materials, such as synthetic hydrogel polymers. Such hydrogel polymers may include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyridine or the like. Other suitable polymers can include hydrolyzed acrylonitrile grafted starch, acrylic acid grafted starch, and isobutylene maleic anhydride copolymers, and mixtures thereof.

The hydrogel polymers are desirably sufficiently crosslinked to render the materials substantially water-insoluble. Cross-linking may, for example, be by irradiation or by covalent, ionic, van der Waals or hydrogen bonding. Suitable materials are available from various commercial vendors, such as Dow Chemical Company, Hoechst-Celanese Corporation and Allied-Colloid. Typically, the high-absorbency material is capable of absorbing at least about 15 times its weight in water, and desirably is capable of absorbing more than about 25 times its weight in water.

The high-absorbency material can be distributed or otherwise incorporated into the absorbent core 60 employing various techniques. For example, the high-absorbency material can be substantially uniformly distributed among the fibers comprising the absorbent core 60. The materials can also be non-uniformly distributed within the absorbent core 60 fibers to form a generally continuous gradient with either an increasing or decreasing concentration of high-absorbency material, as determined by observing the concentration moving inward from the backsheet 58. Alternatively, the high-absorbency material can comprise a discrete layer separate from the fibrous material of the absorbent core 60, or can comprise a discrete layer integral with the absorbent core 60.

The absorbent core 60 may also include a wrap layer (not shown) to help maintain the integrity of the fibrous core. This wrap may comprise a hydrophilic spunbond, meltblown or bonded-carded web material composed of synthetic polymer filaments, such as polypropylene, polyethylene, polyesters or the like or natural polymer filaments such as rayon or cotton. It may also be a creped tissue paper comprised of wood pulp and a wet-strength resin, such as Kymene, a product of Hercules, Inc. of Wilmington, Del.

The waste containment structure 42 most desirably incorporates a backsheet 58 which is vapor pervious and liquid pervious but only to a small degree liquid pervious. It is desirably associated with a cover structure (not shown) which is liquid impervious and which covers or separates the inner 45 waste containment structure from contact with outside surfaces or people.

The crotch area 24 of the waste containment structure 42 could be rendered liquid-impervious by appropriate means such as plastic film, while the upper portion and the waist opening 34 of the waste containment structure 42 could be covered by a liquid-pervious material, to aid in breathability.

The backsheet 58 may comprise a thin, liquid impermeable web or sheet of plastic film such as polyethylene, polypropylene, polyvinyl chloride or similar material. Alternately, the backsheet 58 may comprise a nonwoven, fibrous web which has been suitably constructed and arranged to have low liquid perviousness. Still alternately, the backsheet 58 may comprise a layered or laminated material, such as a thermally bonded plastic film and non-woven web composite. Since the garment 10 is typically intended for active wear, an exposed backsheet or portions thereof, can be made of materials or of a basis weight which is abrasion resistant.

The backsheet 58 may be constructed of a single spun-bonded polypropylene nonwoven web having a basis weight of about 0.5 oz/yd$^2$ (17 gsm) to about 2.0 oz/yd$^2$ (68 gsm). The shorts 14 desirably comprises a material having a basis weight of from about 0.5 oz/yd$^2$ (17 gsm) to about 2.0 oz/yd$^2$ (68 gsm), desirably 1.0 oz./yd$^2$ to 2.0 oz./yd$^2$ at least in the crotch and buttocks regions of the backsheet 58. Lesser basis weights may be used in other regions of the garment 10.

In the waste containment structure 42, the backsheet 58 can also be liquid-pervious, and the cover liquid-impervious, for the same reasons as above (See FIGS. 2 and 3). However, wherein the garment 10 has shorts 14, the crotch area 24 of the waste containment structure 42 could be rendered liquid-impervious by appropriate means such as a plastic film, while the upper portion of the waste containment structure 42 could be covered by a liquid-pervious material, to aid in breathability. In addition, however, the backsheet 58 of the waste containment structure 42 can be made with a vapor pervious material, to allow for some breathability of the structure, while the cover (not shown) is impervious, allowing for fast-drying and containment of any fluid passing through the structure.

The bodyside liner 56 may be any soft, flexible, porous sheet which passes fluids therethrough. Again, the bodyside liner 56 must permit submersion in fresh water, salt water, or treated water and still retain its integrity. The bodyside liner 56 may comprise, for example, a nonwoven web or sheet of a spunbonded, meltblown or bonded-carded web composed of synthetic polymer filaments, such as polypropylene, polyethylene, polyesters or the like, or a web of natural polymer filaments such as rayon or cotton. The bodyside liner 56 has a pore size that readily allows the passage therethrough of liquids, such as urine and other body exudates. The bodyside liner 56 may be selectively embossed or perforated with discrete slits or holes extending therethrough. Optionally, the web or sheet may be treated with a surfactant to aid in liquid transfer. One suitable material for the bodyside liner 56 is a wettable spunbonded polypropylene web produced by the methods and apparatus described in U.S. Pat. No. 4,340,563 issued Jul. 20, 1982, and U.S. Pat. No. 4,405,297 issued Sep. 23, 1983, to Appel et al., which are incorporated herein by reference. The bodyside liner 56 is liquid permeable and is a spunbonded polypropylene nonwoven web having a basis weight of about 0.75 oz/yd$^2$ (25.4 gsm). Suitable adhesives for adhering the laminate layers can be obtained from Findley Adhesives, Inc. of Wauwatosa, Wis.

As described previously, the side panels 26 and 28 may be formed of a material capable of stretching in one direction or capable of stretching in at least two substantially perpendicular directions. One suitable one-directional stretch material is disclosed in U.S. Pat. No. 4,720,415 issued Jan. 19, 1988, to Vander Wielen et al., which is incorporated herein by reference. The one-directional stretch material may comprise a composite material including at least one gatherable web bonded to at least one elongated elastic web.

The elastic web may be an elastic film or nonwoven fibrous elastic webs such as meltblown elastomeric fibrous webs. In one embodiment, the side panels 26 and 28 comprise a stretch bonded laminate formed of a prestretched elastic meltblown inner layer sandwiched between and attached to a pair of spunbond polypropylene nonwoven webs having a basis weight of about 0.4 oz/yd$^2$ (13.6 gsm). Suitable elastic materials can be purchased from the Shell Chemical Company of Houston, Texas under the trade name Kraton. Other suitable one-directional stretch materials are disclosed in U.S. Pat. No. 4,606,964 issued Aug. 19, 1986, to Wideman and U.S. Pat. No. 4,657,802 issued Apr. 14, 1987, to Morman.

The material that can be used for the elastic element which can be used for the side panels 26 and 28 desirably has stretch characteristic in the first direction such that it is capable of from about 10 to about 500 percent elongation and upon release of tension will recover at least 55 percent of its elongation. It is generally desired that the material 40 for use in the side panels 26 and 28 in the first direction be capable of between about 50 and about 300 percent elongation, particularly at least 125 percent elongation and recovery upon release of tension of at least 80 percent of its elongation.

Suitable two-directional stretch materials for the side panels 26 and 28 are disclosed in U.S. Pat. No. 5,114,781 issued May 19, 1992, and U.S. Pat. No. 5,116,662 ssued May 26, 1992, to Morman, which are incorporated herein by eference. A two-directional stretch material may comprise a composite aterial including a neckable material and an elastic sheet, which may be formed by meltblowing or extrusion. Neckable materials are those which ay be constricted in at least one dimension by applying a tensioning force in a direction perpendicular to the desired direction of neck-down, and may include a spunbonded, meltblown or bonded carded web.

The tensioned, necked neckable material may be joined to the elongated elastic sheet at spaced locations arranged in a nonlinear configuration. Another two-directional stretch composite material may comprise one or more layers of reversibly necked material joined to one or more layers of elastic sheet at spaced locations. Reversibly necked materials are those that have been treated, such as with heat, while necked to impart memory to the material so that, when a force is applied to extend the material to its pre-necked dimensions, the treated, necked portions will generally recover to their necked dimensions upon termination of the force.

The leg elastics 36 and 38 and waist elastic members 43 and 45 may be formed of a stretch bonded laminate. In particular, the stretch bonded laminate may comprise at least one nonwoven gatherable layer and an elastic layer. Alternately, the leg elastics 36 and 38 and waist elastic 43 and 45 may be formed of a dry-spun coalesced multi-filament elastomeric thread sold under the tradename LYCRA and available from I.E. Du Pont de Nemours and Company.

Still alternately, the leg elastics 36 and 38 and waist elastic members 43 and 45 may be formed of other typical elastics utilized in the diaper-making art, such as a thin ribbon of elastic material as disclosed in U.S. Pat. No. 4,940,464 issued Jul. 10, 1990, to Van Gompel et al., which is incorporated herein by reference. Elasticity could also be imparted to the longitudinal side sections by extruding a hot melt elastomeric adhesive between the backsheet 58 and the bodyside liner 56. Other suitable elastic gathering means are disclosed in U.S. Pat. Nos. 4,938,754 to Mesek and 4,388,075 to Mesek et al.

The shorts 14 can be desirably constructed of a single layer comprising film layer, nonwoven layer, or any other suitable liquid permeable or liquid impermeable material, desirably having a cloth-like feel. The shorts 14 may be constructed of a single spunbonded polypropylene nonwoven web having a basis weight of about 0.5 oz/yd$^2$ (17 gsm) to about 2.0 oz/yd$^2$ (68 gsm). In the case of garment 10, the shorts 14 desirably comprises a material having a basis weight of from about 0.5 oz/yd$^2$ (17 gsm) to about 2.0 oz/yd$^2$ (68 gsm), desirably 1.0 oz./yd$^2$ to 2.0 oz./yd$^2$ at least in the crotch and buttocks regions of the shorts 14. The shorts 14 typically comprises a material having a basis weight of from about 0.5 oz/yd$^2$ (17 gsm) to about 2.0 oz/yd$^2$ (68 gsm).

The shorts 14 may comprise a second layer of a liquid impermeable film layer suitably joined to the first layer by adhesive. The first layer of the shorts 14 may be spunbonded polypropylene nonwoven web having a basis weight of from about 0.5 oz/yd$^2$ (17 gsm) to about 2.0 oz/yd$^2$ (68 gsm). The second layer of the shorts 14 may be a polyethylene film ranging from 10 about 0.5 to about 1.0 mil in thickness.

The present invention is a continuous process for the manufacture of shorts 14 (or trousers) to be worn about the lower body comprising an outer surface 13 and an opposing inner surface 11, defining a waist opening 34 and two leg openings 93 and 95. The present invention requires at least one web of fabric in a single continuous process to create shorts 14 or trousers. Seaming can be accomplished by use of ultrasonics, heat sealing, adhesives, tape, or sewing, each offering a unique modification to the process.

Figure 4:
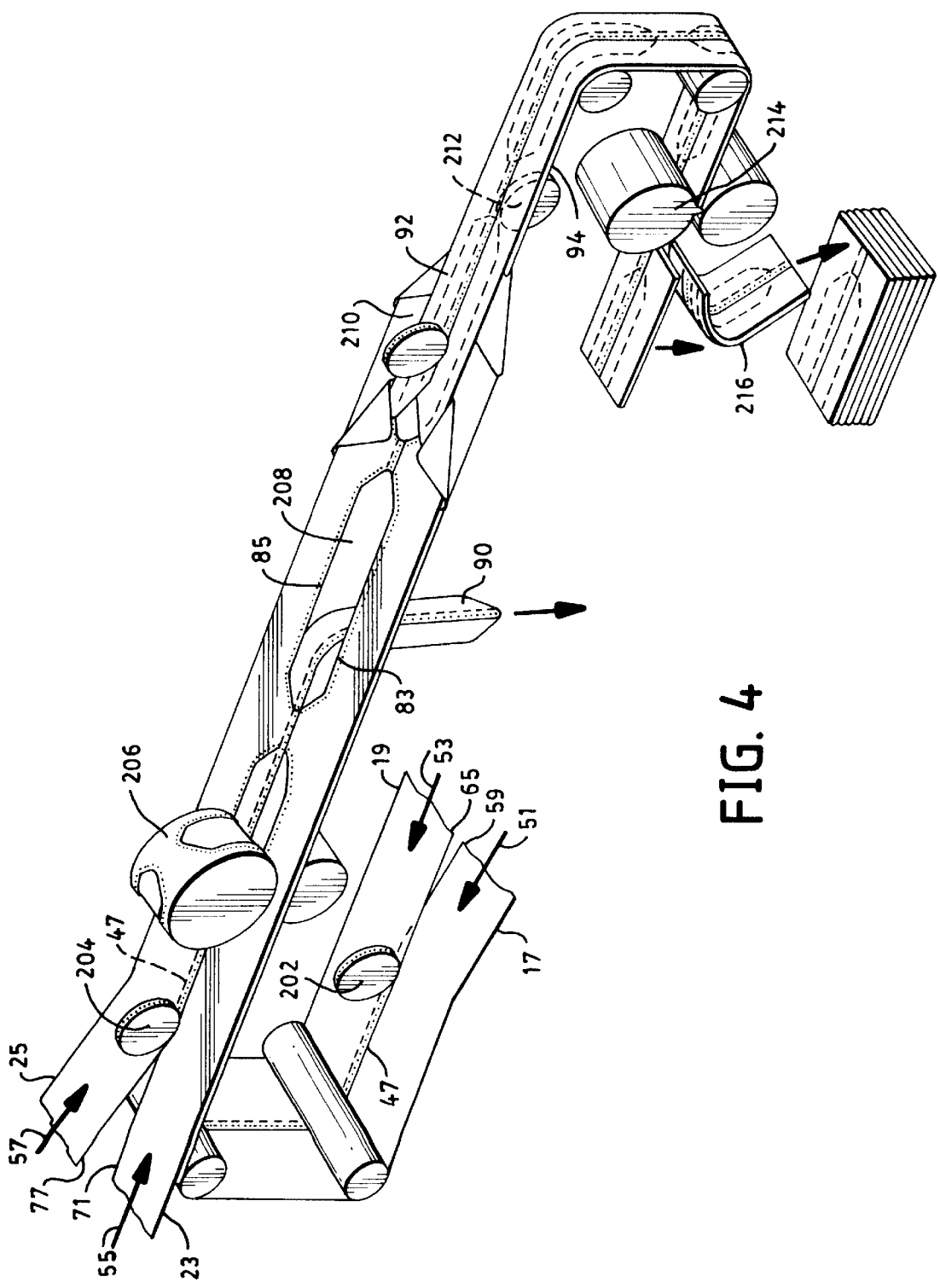
FIG. 4 is a diagram of one embodiment of the present invention.

In one embodiment of the present invention (see FIG. 4), four panels 51, 53, 55, and 57 (also referred to as webs) of sufficient width of fabric to make the garment 10 are combined to produce shorts 14. The desired fabric is nonwoven although any disposable or washable fabric can be used. Two of the panels 51 and 53 of fabric are unwound from rolls and brought together side by side and bonded 202 together at one side edge of each of the panels 51 and 55, defining one half of the inseam seam 47 on the composite web. The desired method of bonding is ultrasonics, although other methods of bonding, such as heat sealing, adhesives, tape, or sewing can be used. The other two panels 53 and 57 are treated 204 in an identical manner, creating a second composite web and the other half of the inseam 47.

The two composite panels (also referred to as front and back panels) of 51 and and 55; and 53 and 57 are then brought together, face to face, resulting in an arrangement made up of two layers of fabric and having four side edges 17, 19, 23, and 25 wherein two side edges (17 and 19; 23 and 25) are adjacent each other, one on top of the other, on each side of the bonding.

The two composite webs (51 and 53, 55 and 57) are then subjected to a crotch bonder 206 wherein a bond, defining center seams 83 and 85, is applied in approximately the shape of an asymmetrical oval near the center of the fabric. (A variety of shapes may be used, symmetrical as well as asymmetrical.) The bonding is applied intermittently and with alternating orientation of top of oval to top of oval and bottom of oval to bottom of oval. (A repeating orientation of top of oval to bottom of oval may also e used.) The distance between the bonding defining the center seams 83 and 85 is varied depending on the desired length of leg covering for the arment. If trousers are desired, more distance is placed between the oval bonding, thereby providing more leg covering. If shorts are desired, less distance is placed between the oval bonding, thereby providing less leg covering.

The interior section 90 of the oval bonding, the portion inside of the center seams 83 and 85, is cut 208, desirably die cut or ultrasonically cut, defining a cavity having a front to back contour to accommodate a human body in the finished garment 10. The interior section 90 can be removed by any method known in the art, desirably a vacuum source.

The top two side edges 17 and 23 are then folded back 210 to meet or overlap. The top side edges 17 and 23 are bonded, defining one side seam 27 and a tubular leg structure 92. The bottom two side edges 19 and 25 are then folded back 212 to meet or overlap. The bottom side edges 19 and 25 are bonded, defining the other side seam 29 and another tubular leg structure 94. If desired, the bottom side edges 19 and 25 could be folded and bonded together before the top side edges 17 and 23 were folded and bonded together. At this point in the process, the fabric has opposing tubular leg structures 92 and 94, one on each side of the center seams 83 and 85, side seams 27 and 29, and the inseam 47.

The fabric is then put through the final cut off knife 214 (or any other cutting device appropriate for this process), defining discrete garments 10 having waist regions 61, 67, 73, and 79, a waist opening 34, and leg openings 93 and 95. The discrete garments 10 are produced in alternating orientation of waist to waist and then leg to leg. Every other garment 10 can be flipped 216 so that the orientation of all of the garments 10 match. In an alternate embodiment, every other garment 10 is transported to a second stack of garments 10.

Each of the garments 10 is now ready for the addition of waist elastics 43 and 45, pant structure 12, waste containment structure 42, or any other feature desired for inclusion in the garments 10.

In another embodiment of the present invention (See FIG. 1), two webs, 51 and 53, of sufficient width of fabric are combined to produce shorts 14. The desired fabric is nonwoven although any disposable or washable fabric can be used. The two webs 51 and 53 of fabric are unwound from rolls and brought together face to face, resulting in an arrangement made up of two layers of fabric and having four side edges 17, 19, 23, and 25 wherein two side edges (17 and 19; 23 and 25) are adjacent each other, one on top of the other, on each side of the bonding defining the inseam 47. The desired method of bonding is ultrasonics, although other methods of bonding, such as heat sealing, adhesives, tape, or sewing can be used.

The fabric is then subjected to a crotch bonder wherein a bond, defining center seams 83 and 85, is applied in approximately the shape of an asymmetrical oval near the center of the fabric. (A variety of shapes may be used, symmetrical as well as asymmetrical.) The bonding is applied intermittently and with alternating orientation of top of oval to top of oval and bottom of oval to bottom of oval. (A repeating orientation of top of oval to bottom of oval may also be used.) The distance between the bonding defining the center seams 83 and 85 is varied depending on the desired length of leg covering for the garment. If trousers are desired, more distance is placed between the oval bonding, thereby providing more leg covering. If shorts are desired, less distance is placed between the oval bonding, thereby providing less leg covering.

The interior section 90 of the oval bonding, the portion inside of the center seams 83 and 85, is cut, desirably die cut or ultrasonically cut, defining a cavity having a front to back contour to accommodate a human body in the finished garment 10. The interior section 90 can be removed by any method known in the art, desirably a vacuum source.

The top two side edges 17 and 23 are then folded back to meet or overlap. The top side edges 17 and 23 are bonded, defining one side seam 27 and a tubular leg structure 92. The bottom two side edges 19 and 25 are then folded back to meet or overlap. The bottom side edges 19 and 25 are bonded, defining the other side seam 29 and another tubular leg structure 94. If desired, the bottom side edges 19 and 25 could be folded and bonded together before the top side edges 17 and 23 were folded and bonded together. At this point in the process, the fabric has opposing tubular leg structures 92 and 94, one on each side of the center seams 83 and 85, side seams 27 and 29, and the inseam 47.

The fabric is then put through the final cut off knife, defining discrete garments 10 each having waist regions 15 and 21, a waist opening 34, and leg openings 93 and 95. The discrete garments 10 are produced in alternating orientation of waist to waist and then leg to leg. Every other garment 10 can be flipped so that the orientation of all of the garments 10 match. In an alternate embodiment, every other garment 10 is transported to a second stack of garments 10.

Each of the garments 10 is now ready for the addition of waist elastics 43 and 45, pant structure 12, waste containment structure 42, or any other feature desired for inclusion in the garments 10.

In still another embodiment of the present invention (See FIG. 1), one web of fabric having sufficient width is processed to produce shorts 14. The desired fabric is nonwoven although any disposable or washable fabric can be used. The one web of fabric is unwound from the roll and slit, or otherwise cut, length-wise into two webs 51 and 53 of fabric. The two webs 51 and 53 are brought together in a face to face orientation, resulting in an arrangement made up of two layers of fabric and having four side edges 17, 19, 23, and 25 wherein two side edges (17 and 19; 23 and 25) are adjacent each other, one on top of the other, on each side of the bonding defining the inseam 47. The desired method of bonding is ultrasonics, although other methods of bonding, such as heat sealing, adhesives, tape, or sewing can be used.

The fabric is then subjected to a crotch bonder wherein a bond, defining the center seams 83 and 85, is applied in approximately the shape of an asymmetrical oval near the center of the fabric. (A variety of shapes may be used, symmetrical as well as asymmetrical.) The bonding is applied intermittently and with alternating orientation of top of oval to top of oval and bottom of oval to bottom of oval. (A repeating orientation of top of oval to bottom of oval may also be used.) The distance between the bonding defining the center seams 83 and 85 is varied depending on the desired length of leg covering for the garment. If trousers are desired, more distance is placed between the oval bonding, thereby providing more leg covering. If shorts are desired, less distance is placed between the oval bonding, thereby providing less leg covering.

The interior section 90 of the oval bonding, the portion inside of the center seams 83 and 85, is cut, desirably die cut or ultrasonically cut, defining a center seam having a front to back contour to accommodate a human body in the finished garment. The interior section can be removed by any method known in the art, desirably a vacuum source.

The top two side edges 17 and 23 are then folded back to meet or overlap. The top side edges 17 and 23 are bonded, defining one side seam 27 and a tubular leg structure 92. The bottom two side edges 19 and 25 are then folded back to meet or overlap. The bottom side edges 19 and 25 are bonded, defining the other side seam 29 and another tubular leg structure 94. If desired, the bottom side edges 19 and 25 could be folded and bonded together before the top side edges 17 and 23 were folded and bonded together. At this point in the process, the fabric has opposing tubular leg structures 92 and 94, one on each side of the center seams 83 and 85, side seams 27 and 29, and the inseam 47.

The fabric is then put through the final cut off knife, defining discrete garments 10 having waist regions 15 and 21, a waist opening 34, and leg openings 93 and 95. The discrete garments 10 are produced in alternating orientation of waist to waist and then leg to leg. Every other garment 10 can be flipped so that the orientation of all of the garments 10 match.

In an alternate embodiment, every other garment 10 is transported to a second stack of garments 10.

Each of the garments is now ready for the addition of waist elastics, pant structure, waste containment structure, or any other feature desired for inclusion.

The present invention relates to a continuous process for the manufacture of a shorts garment comprising:

a. providing four single layer webs 51, 53, 55, and 57 of fabric 3 including two side edges (17, 19, 23, 25, 59, 65, 71, and 77) on each web of fabric 3;

b. aligning two of the four webs (51, 53, 55, and 57) together in a side by side orientation;

c. bonding one side edge 59 and 65 of each of the two webs 51 and 53 in the side by side orientation together, defining at least a portion of an inseam 47 and a first composite web;

d. aligning the remaining two of the four webs (51, 53, 55, and 57) together in a side by side orientation;

e. bonding one side edge 71 and 77 of each of the two webs 55 and 57 in the side by side orientation together, defining at least another portion of the inseam 47 and a second composite web;

f. aligning the first and second composite webs together in the face to face orientation, defining an arrangement having two layers of fabric and two top side edges 17 and 23 and two bottom side edges 19 and 25;

g. intermittently bonding the composite webs wherein the bonding is accomplished in an alternating orientation near the center of the webs, defining center seams 83 and 85 having a specific shape and an interior portion of fabric 3;

h. removing the interior portion of fabric 3, defining a cavity having a front to back contour to accommodate a human body;

i. folding one pair of the side edges 17 and 23 together;
j. bonding the pair of side edges 17 and 23, defining at least one side seam 27 and a tubular leg structure 92;
k. folding the other pair of side edges 19 and 25 together;
l. bonding the other pair of side edges 19 and 25, defining at least another side seam 29 and another tubular leg structure 94; and,
m. cutting the fabric 3, defining discrete garment-sized pieces of fabric 3 wherein each piece of fabric 3 includes at least two side seams 27 and 29, an inseam 47, two tubular leg structures 92 and 94, and a waist opening 34.

The continuous process may further comprise turning every other garment-sized piece of fabric 3 over thereby providing garment-sized pieces of fabric 3 having the same orientation before the garment-sized pieces of fabric 3 are stacked. In the alternative, every other garment-sized pieces of fabric 3 may be placed in a second stack.

Another embodiment of the present invention relates to a continuous process for the manufacture of a shorts garment comprising:
a. providing four multi-layer laminate webs 51, 53, 55, and 57 of fabric 3 including two side edges (17, 19, 23, 25, 59, 65, 71, and 77) on each web of fabric 3;
b. aligning two of the four webs (51, 53, 55, and 57) together in a side by side orientation;
c. bonding one side edge 59 and 65 of each of the two webs 51 and 53 in the side by side orientation together, defining at least a portion of an inseam 47 and a first composite web;
d. aligning the remaining two of the four webs (51, 53, 55, and 57) together in a side by side orientation;
e. bonding one side edge 71 and 77 of each of the two webs 55 and 57 in the side by side orientation together, defining at least another portion of the inseam 47 and a second composite web;
f. aligning the first and second composite webs together in the face to face orientation, defining a arrangement having two layers of fabric and two top side edges 17 and 23 and two bottom side edges 19 and 25;
g. intermittently bonding the composite webs wherein the bonding is accomplished in an alternating orientation near the center of the webs, defining center seams 83 and 85 having a specific shape and an interior portion of fabric 3;
h. removing the interior portion of fabric 3, defining a cavity having a front to back contour to accommodate a human body;
i. folding one pair of the side edges 17 and 23 together;
j. bonding the pair of side edges 17 and 23, defining at least one side seam 27 and a tubular leg structure 92;
k. folding the other pair of side edges 19 and 25 together;
l. bonding the other pair of side edges 19 and 25, defining at least another side seam 29 and another tubular leg structure 94; and,
m. cutting the fabric 3, defining discrete garment-sized pieces of fabric 3 wherein each piece of fabric 3 includes at least two side seams 27 and 29, an inseam 47, two tubular leg structures 92 and 94, and a waist opening 34.

The present invention also relates to a continuous process for the manufacture of a shorts garment comprising:
a. providing two single layer webs 51 and 53 of fabric 3 including two side edges (17, 19, 23, and 25) on each web 51 and 53 of fabric 3;
b. aligning the two webs 51 and 53 together in a face to face orientation, defining an arrangement having two layers of fabric and one pair of top side edges 17 and 23 and one pair of bottom side edges 19 and 25;
c. intermittently bonding the webs 51 and 53 wherein the bonding is accomplished in an alternating orientation near the center of the fabric 3, defining center seams 83 and 85 having a specific shape and an interior portion of fabric 3;
d. removing the interior portion of fabric 3, defining a cavity having a front to back contour to accommodate a human body;
e. folding one pair of side edges 17 and 23 together;
f. bonding the pair of side edges 17 and 23, defining at least one side seam 27 and a tubular leg structure 92;
g. folding the other pair of side edges 19 and 25 together;
h. bonding the other pair side edges 19 and 25, defining at least another side seam 29 and another tubular leg structure 94; and,
i. cutting the fabric 3, defining discrete garmentsized pieces of fabric 3 wherein each piece of fabric 3 includes at least two side seams 27 and 29, an inseam 47, two tubular leg structures 92 and 94, and a waist opening 34.

One embodiment of the present invention relates to a continuous process for the manufacture of a shorts garment comprising:
a. providing two multi-layer laminate webs 51 and 53 of fabric 3 including two side edges (17, 19, 23, and 25) on each web 51 and 53 of fabric 3;
b. aligning the two webs 51 and 53 together in a face to face orientation, defining an arrangement having two layers of fabric and one pair of top side edges 17 and 23 and one pair of bottom side edges 19 and 25;
c. intermittently bonding the webs 51 and 53 wherein the bonding is accomplished in an alternating orientation near the center of the fabric 3, defining center seams 83 and 85 having a specific shape and an interior portion of fabric 3;
d. removing the interior portion of fabric 3, defining a cavity having a front to back contour to accommodate a human body;
e. folding one pair of side edges 17 and 23 together;
f. bonding the pair of side edges 17 and 23, defining at least one side seam 27 and a tubular leg structure 92;
g. folding the other pair of side edges 19 and 25 together;
h. bonding the other pair side edges 19 and 25, defining at least another side seam 29 and another tubular leg structure 94; and,
i. cutting the fabric 3, defining discrete garmentsized pieces of fabric 3 wherein each piece of fabric 3 includes at least two side seams 27 and 29, an inseam 47, two tubular leg structures 92 and 94, and a waist opening 34.

The present invention also relates to a continuous process for the manufacture of a shorts garment comprising:
a. providing one single layer web of fabric 3;
b. slitting the web of fabric length-wise thereby forming two single layer webs 51 and 53 of fabric 3 including two side edges (17, 19, 23, and 25) on each web 51 and 53 of fabric 3;
c. aligning the two webs 51 and 53 together in a face to face orientation, defining an arrangement having two layers of fabric and one pair of top side edges 17 and 23 and one pair of bottom side edges 19 and 25;

d. intermittently bonding the webs 51 and 53 wherein the bonding is accomplished in an alternating orientation near the center of the fabric 3, defining center seams 83 and 85 having a specific shape and an interior portion of fabric 3;

e. removing the interior portion of fabric 3, defining a cavity having a front to back contour to accommodate a human body;

f. folding one pair of side edges 17 and 23 together;

g. bonding the pair of side edges 17 and 23, defining at least one side seam 27 and a tubular leg structure 92;

h. folding the other pair of side edges 19 and 25 together;

i. bonding the other pair side edges 19 and 25, defining at least another side seam 29 and another tubular leg structure 94; and, j. cutting the fabric 3, defining discrete garmentsized pieces of fabric 3 wherein each piece of fabric 3 includes at least two side seams 27 and 29, an inseam 47, two tubular leg structures 92 and 94, and a waist opening 34.

Another embodiment of the present invention relates to a continuous process for the manufacture of a shorts garment comprising:

a. providing one multi-layer laminate web of fabric;

b. slitting the web of fabric length-wise thereby forming two single layer webs 51 and 53 of fabric 3 including two side edges (17, 19, 23, and 25) on each web 51 and 53 of fabric 3;

c. aligning the two webs 51 and 53 together in a face to face orientation, defining an arrangement having two layers of fabric and one pair of top side edges 17 and 23 and one pair of bottom side edges 19 and 25;

d. intermittently bonding the webs 51 and 53 wherein the bonding is accomplished in an alternating orientation near the center of the fabric 3, defining center seams 83 and 85 having a specific shape and an interior portion of fabric 3;

e. removing the interior portion of fabric 3, defining a cavity having a front to back contour to accommodate a human body;

f. folding one pair of side edges 17 and 23 together;

g. bonding the pair of side edges 17 and 23, defining at least one side seam 27 and a tubular leg structure 92;

h. folding the other pair of side edges 19 and 25 together;

i. bonding the other pair side edges 19 and 25, defining at least another side seam 29 and another tubular leg structure 94; and, j. cutting the fabric 3, defining discrete garmentsized pieces of fabric 3 wherein each piece of fabric 3 includes at least two side seams 27 and 29, an inseam 47, two tubular leg structures 92 and 94, and a waist opening 34.

The foregoing detailed description has been for the purpose of illustration. Thus, a number of modifications and changes may be made without departing from the spirit and scope of the present invention. For instance, alternative or optional features described as part of one embodiment can be used to yield another embodiment. Additionally, only one rather than both ends of the waste containment structure can be elastically connected to the cover. Therefore, the invention should not be limited by the specific embodiments described, but only by the claims.

The materials of which can be used in the process are any materials, disposable or washable, specifically desired by the user or manufacturer. Numerous examples of materials used in constructing the garment 10 are described in the aforementioned U.S. patents and patent applications incorporated by reference herein.

What is claimed is:

1. A continuous process for the manufacture of a shorts garment comprising:

a. providing four single layer webs of fabric including two side edges on each web of fabric;

b. aligning two of the four webs together in a side by side orientation;

c. bonding one side edge of each of the two webs in the side by side orientation together, defining at least a portion of an inseam and a first composite web;

d. aligning the remaining two of the four webs together in a side by side orientation;

e. bonding one side edge of each of the two webs in the side by side orientation together, defining at least another portion of the inseam and a second composite web;

f. aligning the first and second composite webs together in the face to face orientation, defining a arrangement having two layers of fabric and two top side edges and two bottom side edges;

g. intermittently bonding the composite webs wherein the bonding is accomplished in an alternating orientation near the center of the webs, defining center seams having a specific shape and an interior portion of fabric;

h. removing the interior portion of fabric, defining a cavity having a front to back contour to accommodate a human body;

i. folding one pair of the side edges together;

j. bonding the pair of side edges, defining at least one side seam and a tubular leg structure;

k. folding the other pair of side edges together;

l. bonding the other pair of side edges, defining at least another side seam and another tubular leg structure; and, m. cutting the fabric, defining discrete garmentsized pieces of fabric wherein each piece of fabric includes at least two side seams, an inseam, two tubular leg structures, and a waist opening.

2. The continuous process according to claim 1, further comprising turning every other garment-sized piece of fabric over thereby providing garment-sized pieces of fabric having the same orientation before the garment-sized pieces of fabric are stacked.

3. The continuous process according to claim 1, further comprising placing every other garment-sized pieces of fabric in a second stack.

4. A continuous process for the manufacture of a shorts garment comprising:

a. providing four multi-layer laminate webs of fabric including two side edges on each web of fabric;

b. aligning two of the four webs together in a side by side orientation;

c. bonding one side edge of each of the two webs in the side by side orientation together, defining at least a portion of an inseam and a first composite web;

d. aligning the remaining two of the four webs together in a side by side orientation;

e. bonding one side edge of each of the two webs in the side by side orientation together, defining at least another portion of the inseam and a second composite web;

f. aligning the first and second composite webs together in the face to face orientation, defining an arrangement having two layers of multi-layer laminate of fabric and one pair of top side edges and one pair of bottom side edges;

g. intermittently bonding the webs wherein the bonding is accomplished in an alternating orientation near the center of the single web, defining center seams having a specific shape and an interior portion of fabric;

h. removing the interior portion of fabric, defining a cavity having a front to back contour to accommodate a human body;

i. folding one pair of the side edges together;

j. bonding the pair of side edges, defining at least one side seam and a tubular leg structure;

k. folding the other pair of side edges together;

l. bonding the other pair of side edges, defining at least another side seam and another tubular leg structure; and, m. cutting the fabric, defining discrete garmentsized pieces of fabric wherein each piece of fabric includes at least two side seams, an inseam, two tubular leg structures, and a waist opening.

5. The continuous process according to claim 4, further comprising turning every other garment-sized piece of fabric over thereby providing garment-sized pieces of fabric having the same orientation before the garment-sized pieces of fabric are stacked.

6. The continuous process according to claim 4, further comprising placing every other garment-sized pieces of fabric in a second stack.

7. A continuous process for the manufacture of a shorts garment comprising:

a. providing two single layer webs of fabric including two side edges on each web of fabric;

b. aligning the two webs together in a face to face orientation, defining an arrangement having two layers of fabric and one pair of top side edges and one pair of bottom side edges;

c. intermittently bonding the webs wherein the bonding is accomplished in an alternating orientation near the center of the single web, defining center seams having a specific shape and an interior portion of fabric;

d. removing the interior portion of fabric, defining a cavity having a front to back contour to accommodate a human body;

e. folding one pair of side edges together;

f. bonding the pair of side edges, defining at least one side seam and a tubular leg structure;

g. folding the other pair of side edges together;

h. bonding the other pair side edges, defining at least another side seam and another tubular leg structure; and, i. cutting the fabric, defining discrete garmentsized pieces of fabric wherein each piece of fabric includes at least two side seams, an inseam, two tubular leg structures, and a waist opening.

8. The continuous process according to claim 7, further comprising turning every other garment-sized piece of fabric over thereby providing garment-sized pieces of fabric having the same orientation before the garment-sized pieces of fabric are stacked.

9. The continuous process according to claim 7, further comprising placing every other garment-sized pieces of fabric in a second stack.

10. A continuous process for the manufacture of a shorts garment comprising:

a. providing two multi-layer laminate webs of fabric including two side edges on each web of fabric;

b. aligning the two webs together in a face to face orientation, defining an arrangement having two layers of multi-layer laminate of fabric and one pair of top side edges and one pair of bottom side edges;

c. intermittently bonding the webs wherein the bonding is accomplished in an alternating orientation near the center of the single web, defining center seams having a specific shape and an interior portion of fabric;

d. removing the interior portion of fabric, defining a cavity having a front to back contour to accommodate a human body;

e. folding one pair of side edges together;

f. bonding the pair of side edges, defining at least one side seam and a tubular leg structure;

g. folding the other pair of side edges together;

h. bonding the other pair side edges, defining at least another side seam and another tubular leg structure; and, i. cutting the fabric, defining discrete garmentsized pieces of fabric wherein each piece of fabric includes at least two side seams, an inseam, two tubular leg structures, and a waist opening.

11. The continuous process according to claim 10, further comprising turning every other garment-sized piece of fabric over thereby providing garment-sized pieces of fabric having the same orientation before the garment-sized pieces of fabric are stacked.

12. The continuous process according to claim 10, further comprising placing every other garment-sized pieces of fabric in a second stack.

13. A continuous process for the manufacture of a shorts garment comprising:

a. providing one single layer web of fabric;

b. slitting the web of fabric length-wise thereby forming two single layer webs of fabric including two side edges on each web of fabric;

c. aligning the two webs together in a face to face orientation, defining an arrangement having two layers of fabric and one pair of top side edges and one pair of bottom side edges;

d. intermittently bonding the webs wherein the bonding is accomplished in an alternating orientation near the center of the single web, defining center seams having a specific shape and an interior portion of fabric;

e. removing the interior portion of fabric, defining a cavity having a front to back contour to accommodate a human body;

f. folding one pair of side edges together;

g. bonding the pair of side edges, defining at least one side seam and a tubular leg structure;

h. folding the other pair of side edges together;

i. bonding the other pair side edges, defining at least another side seam and another tubular leg structure; and, j. cutting the fabric, defining discrete garmentsized pieces of fabric wherein each piece of fabric includes at least two side seams, an inseam, two tubular leg structures, and a waist opening.

14. The continuous process according to claim 13, further comprising turning every other garment-sized piece of fabric over thereby providing garment-sized pieces of fabric having the same orientation before the garment-sized pieces of fabric are stacked.

15. The continuous process according to claim 13, further comprising placing every other garment-sized pieces of fabric in a second stack.

16. A continuous process for the manufacture of a shorts garment comprising:
   a. providing one multi-layer laminate web of fabric;
   b. slitting the web of fabric length-wise thereby forming two single layer webs of fabric including two side edges on each web of fabric;
   c. aligning the two webs together in a face to face orientation, defining an arrangement having two layers of multi-layer laminate fabric and one pair of top side edges and one pair of bottom side edges;
   e. intermittently bonding the webs wherein the bonding is accomplished in an alternating orientation near the center of the single web, defining center seams having a specific shape and an interior portion of fabric;
   f. removing the interior portion of fabric, defining a cavity having a front to back contour to accommodate a human body;
   g. folding one pair of side edges together;
   h. bonding the pair of side edges, defining at least one side seam and a tubular leg structure;
   i. folding the other pair of side edges together;
   j. bonding the other pair side edges, defining at least another side seam and another tubular leg structure; and,
   k. cutting the fabric, defining discrete garmentsized pieces of fabric wherein each piece of fabric includes at least two side seams, an inseam, two tubular leg structures, and a waist opening.

17. The continuous process according to claim 16, further comprising turning every other garment-sized piece of fabric over thereby providing garment-sized pieces of fabric having the same orientation before the garment-sized pieces of fabric are stacked.

18. The continuous process according to claim 16, further comprising placing every other garment-sized pieces of fabric in a second stack.

* * * * *

UNITED STATES PATENT AND TRADEMARK OFFICE
CERTIFICATE OF CORRECTION

PATENT NO. : 6,192,521 B1
DATED : February 27, 2001
INVENTOR(S) : J.L. Aberts et al.

It is certified that error appears in the above-identified patent and that said Letters Patent is hereby corrected as shown below:

Column 1,
Line 58, delete "a" and substitute -- an -- therefor.

Column 2,
Line 60, delete "boding" and substitute -- bonding -- therefor.

Column 11,
Line 11, delete "45".
Line 46, delete "ssued" and substitute -- issued -- therefor.
Line 48, delete "eference" and substitute -- reference -- therefor.
Line 49, delete aterial" and substitute -- material -- therefor.
Line 51, delete "ay" and substitute -- may -- therefor.

Column 13,
Line 41, delete "10".
Line 66, delete the second "and".

Column 14,
Line 13, delete "e" and substitute -- be -- therefor.
Line 16, delete "arment" and substitute -- garment -- therefor.
Line 54, delete "1" and substitute -- 1a -- therefor.

Column 15,
Line 46, delete "1" and substitute -- 1a -- therefor.

Column 17,
Line 39, delete "a" and substitute -- an -- therefor.

UNITED STATES PATENT AND TRADEMARK OFFICE
CERTIFICATE OF CORRECTION

PATENT NO. : 6,192,521 B1
DATED : February 27, 2001
INVENTOR(S) : J.L. Aberts et al.

It is certified that error appears in the above-identified patent and that said Letters Patent is hereby corrected as shown below:

Column 20,
Line 23, delete "a" and substitute -- an -- therefor.

Signed and Sealed this

Eighth Day of January, 2002

Attest:

JAMES E. ROGAN
*Attesting Officer*     *Director of the United States Patent and Trademark Office*